United States Patent
DeFilippi et al.

(10) Patent No.: US 7,744,856 B2
(45) Date of Patent: Jun. 29, 2010

(54) FORMULATIONS WITH FERULOYL GLYCERIDES AND METHODS OF PREPARATION

(75) Inventors: Louis J. DeFilippi, Palatine, IL (US); Steven G. Grall, Lemont, IL (US); James F. Kinney, Ramsey, NJ (US); Joseph A. Laszlo, Peoria, IL (US); David L. Compton, Peoria, IL (US)

(73) Assignee: Biotech Research and Development Corporation, Peoria, IL (US)

( * ) Notice: Subject to any disclaimer, the term of this patent is extended or adjusted under 35 U.S.C. 154(b) by 0 days.

(21) Appl. No.: 11/771,843

(22) Filed: Jun. 29, 2007

(65) Prior Publication Data

US 2008/0050321 A1    Feb. 28, 2008

Related U.S. Application Data

(63) Continuation-in-part of application No. 11/425,094, filed on Jun. 19, 2006, and a continuation-in-part of application No. 11/425,096, filed on Jun. 19, 2006, now Pat. No. 7,572,610.

(60) Provisional application No. 60/817,537, filed on Jun. 29, 2006, provisional application No. 60/723,209, filed on Oct. 3, 2005.

(51) Int. Cl.
A61K 8/00 (2006.01)
A61K 8/18 (2006.01)
A61Q 17/04 (2006.01)

(52) U.S. Cl. .................................................. 424/59
(58) Field of Classification Search .................... 424/59
See application file for complete search history.

(56) References Cited

U.S. PATENT DOCUMENTS

| | | | |
|---|---|---|---|
| 3,153,659 A | 10/1964 | King | |
| 5,155,244 A | 10/1992 | Greene et al. | |
| 5,380,890 A | 1/1995 | Greene et al. | |
| 5,614,648 A | 3/1997 | Greene et al. | |
| 5,683,683 A * | 11/1997 | Scafidi | 424/70.19 |
| 5,817,299 A * | 10/1998 | Manirazman | 424/59 |
| 5,902,591 A * | 5/1999 | Herstein | 424/401 |
| 6,013,270 A * | 1/2000 | Hargraves et al. | 424/401 |
| 6,346,236 B1 | 2/2002 | Compton et al. | |
| 6,372,234 B1 * | 4/2002 | Deckers et al. | 424/401 |
| 6,565,865 B2 | 5/2003 | Bekele | |
| 6,890,520 B2 | 5/2005 | Taniguchi et al. | |
| 2001/0021375 A1 | 9/2001 | Hossel et al. | |
| 2004/0258635 A1 | 12/2004 | Harry-O'kuru et al. | |
| 2004/0258743 A1 | 12/2004 | Compton et al. | |
| 2005/0096340 A1 | 5/2005 | Zhang et al. | |
| 2007/0077214 A1 | 4/2007 | Laszlo et al. | |
| 2007/0077636 A1 | 4/2007 | Laszlo et al. | |

FOREIGN PATENT DOCUMENTS

| | | |
|---|---|---|
| WO | 9533706 A1 | 12/1995 |
| WO | 01/72683 A1 | 10/2001 |
| WO | 2007041424 A1 | 4/2007 |

OTHER PUBLICATIONS

Lin, et al. "Ferulic Acid Stabilizes a Solution of Vitamin C and E and Doubles its Photoprotection of Skin" J Invest Demartol 2005, v. 125, pp. 826.
International Search Report for PCT/US07/72557, dated Feb. 27, 2008, pp. 1-3.
Joseph A. Laszlo, et al. "Packed-Bed Bioreactor Synthesis of Feruloylated Monoacyl- and Diacylglycerols: Clean Production of a "Green" Sunscreen," Green Chemistry, 2003, vol. 5, pp. 382-386.
K. Warner, et al. "Addition of Ferulic Acid, Ethyl Ferulate, and Feruloylated Monoacyl- and Diacylglycerols to Salad Oils and Frying Oils," Journal of American Oil Chemists' Society, vol. 82, No. 9, 2005, pp. 647-652.
Daniela I. Batovska, et al. "Synthesis of Some Phenylpropanoid Monoglycerides Via the Mitsunobu Protocol," Molecules, vol. 10, Mar. 2005, pp. 552-558.
Raymond Cooper, et al. "New Phenolic Diglycerides From Aegilops Ovata," Phytochemistry, vol. 17, 1978, pp. 1673-1675.
Yoshihiro Mimaki, et al. "Steroidal Saponins From the Bulbs of Lilium Brownii," Phytochemistry, vol. 29, No. 7, 1990, pp. 2267-2271.

(Continued)

Primary Examiner—Johann R Richter
Assistant Examiner—Luke E Karpinski
(74) Attorney, Agent, or Firm—Banner & Witcoff, Ltd.

(57) ABSTRACT

A product for topical application comprising a chemical composition comprising in combination a linker agent and a compound comprising at least one UV-absorbing chromophore, wherein the linker agent is characterized by the general formula:

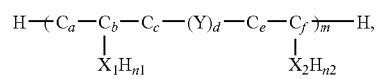

wherein:
$X_1$ and $X_2$ are the same or different, and at least one of $X_1$ or $X_2$ is a functional group that bonds with the compound comprising at least one UV-absorbing chromophore, and $b+f \geq 2$;
Y comprises an O, N, or S that is substituted or unsubstituted;
each a, b, c, e and f is $\geq 0$ and $a+b+c+e+f \geq 2$;
d is 0 or 1;
n1 and n2 represent the number of hydrogen atoms required to complete the undesignated valencies; and
m ranges from 1 to about 100 and each individual m unit may be the same or different,
and a topically acceptable agent that is different from the linker agent and the compound comprising at least one UV-absorbing chromophore.

10 Claims, No Drawings

OTHER PUBLICATIONS

Dae Sik Jang, et al. "Constituents of Asparagus Officinalis Evaluated for Inhibitory Activity Against Cyclooxygenase-2" Journal of Agricultural and Food Chemistry, vol. 52, 2004, pp. 2218-2222.

B. Guyot, et al. "Esterification of Phenolic Acids From Green Coffee With an Immobilized Lipase From *Candida antarctica* in Solvent-Free Medium," Biotechnology Letters, vol. 19, No. 6, 1997, pp. 529-532.

Safari Mohammad, et al. "Enzymatic Synthesis of Structured Phenolic Lipids by Incorporation of Selected Phenolic Acids Into Triolein," Database Biosis (Online) Biosciences Information Service, Biosis No. 200600603731, Biocatalysts and Biotransformation, vol. 24, No. 4, Jul. 2006, pp. 272-279.

Tsuchiyama Moriyasu, et al. "Esterification of Ferulic Acid With Polyols Using a Ferulic Esterase From Aspergillus Niger," Database Biosis (Online) Biosciences Information Service, Biosis No. 200600438669, Biochimica et Biophysica Acta, vol. 1761, No. 7, Jul. 2006, pp. 1071-1079.

Joseph A. Lazio, et al. "Enzymatic Glycerolysis and Transesterification of Vegetable Oil for Enhanced Production of Feruloylated Glycerols," Database Biosis (Online) Biosciences Information Service, Biosis No. 200600562491, Journal of American Oil Chemists' Society, vol. 83, No. 9, 2006, pp. 765-770.

Holser, R.A. et al., "Preparation and Characterization of 4-Methoxy Cinnamoyl Glycerol," J. Am Oil Chem Soc, 2008, pp. 347-351, vol. 85, Springer AOCS, USA.

Holser Ronald A., "Kinetics of Cinnamoyl Glycerol Formation," J. Am Oil Chem Soc, 2008, pp. 221-225, vol. 85, Springer AOCS, USA.

Sabally, Kebba et al., "Lipase-catalyzed transesterification of dihydrocaffeic acid with flaxseed oil for the synthesis of phenolic lipids," Journal of Biotechnology, 2007, pp. 167-176, vol. 127, Elsevier B.V.

Sun, Shangde et al., "A novel, two consecutive enzyme synthesis of feruloylated monoacyl- and diacyl-glycerols in a solvent-free system," Biotechol Lett, 2007, pp. 1947-1950, vol. 29, Springer Science+ Business Media B.V.

Sun, Shangde et al., "Solvent-free enzymatic synthesis of feruloylated diacylglycerols and kinetic study," Journal of Molecular Catalysis B: Enzymatic, 2007, pp. 1-21.

Sun, Shangde et al., "Solvent-free synthesis of glyceryl ferulate using a commercial microbial lipase," Biotechnol Lett, 2007, pp. 945-949, vol. 29, Springer Science+ Business Media B.V.

Xin, Jia-Ying et al., "Lipase-catalyzed synthesis of ferulyl oleins in solvent-free medium," Food Chemistry, 2009, pp. 640-645, vol. 112, Elsevier Ltd.

Hatfield, Ronald D. et al., "Synthesis of Methyl 5-O-trans-Feruloyl-a-L-arabinofuranoside and Its Use as a Substrate to Assess Feruloyl Esterase Activity," Analytical Biochemistry, 1991, pp. 25-33, vol. 194, Academic Press, Inc.

Helm, Richard F. et al., "Synthesis of feruloylated and p-coumaroylated methyl glycosides," Carbohydrate Research, 1992, pp. 183-194, vol. 229, Elsevier Science Publishers.

Lu, Fachuang, et al., "Facile Synthesis of 4-Hydroxycinnamyl p-Coumarates," J. Agric. Food Chem., 1998, pp. 2911-2913, vol. 46, No. 8, American Chemical Society.

Compton, David L. et al., "Lipase-Catalyzed Synthesis of Ferulate Esters," JAOCS, 2000, pp. 513-519, vol. 77, No. 5, AOCS Press.

Torres, Carlos F. et al., "Lipase-catalyzed synthesis of designer acylglycerols rich in residues of eicosapentaenoic, docosahexaenoic, conjugated linoleic, and/or stearic acids," Eur. J. Lipid Sci. Technol., 2003, pp. 614-623, vol. 105, WILEY-VCH Verlag GmbH & Co., KGaA, Weinheim.

International Preliminary Examination Report for PCT/US07/72557, mailed on Oct. 7, 2009, pp. 1-12.

* cited by examiner

FORMULATIONS WITH FERULOYL GLYCERIDES AND METHODS OF PREPARATION

CROSS-REFERENCE TO RELATED APPLICATIONS

This application claims priority to U.S. Provisional Application Ser. No. 60/723,209, filed Oct. 3, 2005, and entitled "Accelerated Feruloylation of Vegetable Oils," and is a continuation-in-part of both U.S. Ser. No. 11/425,094, filed Jun. 19, 2006, and entitled "Compositions Comprising A UV-Absorbing Chromophore," and of U.S. patent application Ser. No. 11/425,096, filed Jun. 19, 2006, and entitled "Methods of Making Compositions Comprising A UV-Absorbing Chromophore," and claims priority to U.S. Provisional Application No. 60/817,537, filed on Jun. 29, 2006, and entitled "Formulations with Feruloyl Glycerides and Methods of Preparation, all of which are hereby incorporated herein their entireties.

FIELD OF THE INVENTION

The present invention relates to feruloyl glycerides, their method of preparation, and their use in personal care consumer product applications.

BACKGROUND OF THE INVENTION

Feruloyl-substituted and coumaryl-substituted acylglycerols, their method of preparation through the transesterfication of a triglyceride and a ferulic or coumaric ester, and the use of these compounds as sunscreen ingredients is taught in U.S. Pat. No. 6,346,236, which incorporated herein by reference in its entirety.

SUMMARY OF THE INVENTION

Feruloyl glycerides have been discovered and are the subject matter of pending patent applications. See U.S. Provisional Application Ser. No. 60/723,209, filed Oct. 3, 2005 and entitled "Accelerated Feruloylation of Vegetable Oils," which is incorporated herein by reference, and U.S. patent application Ser. No. 11/425,094, filed Jun. 19, 2006, and entitled "Compositions Comprising A UV-Absorbing Chromophore," and U.S. patent application Ser. No. 11/425,096, filed Jun. 19, 2006, and entitled "Methods of Making Compositions Comprising A UV-Absorbing Chromophore," all of which are incorporated by reference herein in their entireties.

It has been discovered that these compounds provide a springboard into a broad spectrum of formulating applications within the personal care and over-the-counter (OTC) product categories. Unlike traditional ingredients, the feruloyl glycerides of the present invention have multi-functional properties, and as a result provide a multitude of unexpected benefits and superior characteristics to skin, hair, bath, dental and OTC products.

Disclosed herein products for topical application comprising a chemical composition comprising a linker agent and a compound comprising at least one UV-absorbing chromophore, wherein the linker agent is characterized by the general formula:

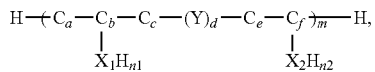

wherein $X_1$ and $X_2$ are the same or different, and at least one of $X_1$ or $X_2$ is a functional group that bonds with the compound comprising at least one UV-absorbing chromophore, and $b+f \geq 2$, Y comprises an O, N, or S that is substituted or unsubstituted, each a, b, c, e and f is $\geq 0$ and $a+b+c+e+f \geq 7$, d is 0 or 1, n1 and n2 represent the number of hydrogen atoms required to complete the undesignated valencies, and m ranges from 1 to about 100 and each individual m unit may be the same or different, and a topically acceptable agent that is different from the linker agent and the compound comprising at least one UV-absorbing chromophore.

Also disclosed herein are products for topical application comprising formulations comprising a fat soluble composition comprising a mono or diacylglycerol esterified with a plant-derived functional group comprising an aromatic species, an unsaturated isoprenoid, an unsaturated terpenoid, a hindered hydroxy-substituted cinnamic acid, an unhindered hydroxy-substituted cinnamic acid or combinations thereof, and a topically acceptable agent that is different from the fat soluble composition.

Also disclosed herein are products for topical application comprising formulations comprising a fat-soluble composition, comprising a glycerol esterified with a plant-derived functional group comprising maleanilic acid, homovanillic acid, folic acid, crocetin, coumaric acid, caffeic acid, ferulic acid, sinapic acid (sinapinic acid), derivatives thereof or combinations thereof, wherein the esterified glycerol includes at least two plant-derived functional groups, and a topically acceptable agent that is different from fat-soluble composition.

Also disclosed herein products for topical application comprising formulations comprising a chemical composition comprising a linker agent and a compound comprising at least one UV absorbing chromophore, wherein the linker agent is characterized by the general formula:

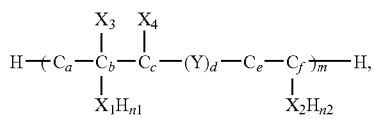

wherein $X_1$ and $X_2$ are the same or different at least one of $X_1$ or $X_2$ is a functional group that bonds with the compound comprising at least one UV-absorbing chromophore, and $b+f \geq 2$, $X_3$ and $X_4$ are the same or different and $X_3$, $X_4$ or both is a hydrophobic moiety, Y comprises an O, N, or S that is substituted or unsubstituted, each a, b, c, e and f is $\geq 0$ and $a+b+c+e+f \geq 2$, d is 0 or 1, n1 and n2 represent the number of hydrogen atoms required to complete the undesignated valencies, and m ranges from 1 to about 100 and each individual m unit may be the same or different, and a topically acceptable agent that is different from the linker agent and the compound comprising at least one UV-absorbing chromophore.

Also disclosed herein are products for topical application comprising formulations comprising a chemical composition comprising at least two compounds having the general formula:

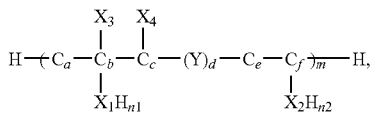

wherein $X_1$ and $X_2$ are different at least one of $X_1$ or $X_2$ is a functional group that bonds with a compound comprising at least one UV-absorbing chromophore, and $b+f \geq 2$, $X_3$ and $X_4$ are the same or different and $X_3$, $X_4$ or both is a hydrophobic moiety, Y comprises an O, N, or S that is substituted or unsubstituted, each a, b, c, e and f is $\geq 0$ and $a+b+c+e+f \geq 2$, d is 0 or 1, n1 and n2 represent the number of hydrogen atoms required to complete the undesignated valencies, m ranges from 1 to about 100 and each individual m unit may be the same or different, and wherein the compound comprising at least one UV-absorbing chromophore comprises a phytochemical which further comprises an aromatic species, an unsaturated isoprenoid, an unsaturated terpenoid, a hindered hydroxy-substituted cinnamic acid, an unhindered hydroxy-substituted cinnamic acid or combinations thereof, and a topically acceptable agent that is different from the chemical composition comprising at least two compounds.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

DETAILED DESCRIPTION OF EMBODIMENTS

The formulations of the present invention comprise compounds that are described in U.S. patent application Ser. No. 11/425,094, filed Jun. 19, 2006, and entitled "Compositions Comprising A UV-Absorbing Chromophore," and U.S. patent application Ser. No. 11/425,096, filed Jun. 19, 2006, and entitled "Methods of Making Compositions Comprising A UV-Absorbing Chromophore," both of which are incorporated by reference herein in their entireties.

Described below are several product applications for formulations in accordance with the present invention. Each application has been made and tested in blind coded consumer panel samples. These tests demonstrate superior aesthetic and consumer product characteristics arising from the compounds of the present invention. The product applications for using the feruloyl glycerides in the present invention are not limited to examples cited herein. Rather, these examples are evidence of the unique multi-functional benefits that are provided with the use of these naturally derived mono, di and triglycerides.

Before offering detailed formula examples of product applications wherein superior consumer benefits have been realized through the use of feruloyl glycerides, it is worth a few sentences to review the multi-functional attributes that this material has exhibited.

The feruloyl glycerides used in accordance with the present invention are lipophilic in nature, with a unique fingerprint of saturated and unsaturated esterified fatty acids, feruloyl esters and hydroxyl groups. As such, the feruloyl glycerides of the present invention are miscible with many other oil-like substances, have a high kb (kauri butanol) value and solvent power, and have excellent skin and hair absorption and/or penetration characteristics. The feruloyl glycerides of the present invention provide the skin with superior moisture barrier properties, add light reflective or radiance characteristics to dull, dry skin, absorb both Ultra Violet A and B wavelengths of sunlight, offer the skin superior antioxidant protection at various levels within the epidermis, and improve the emollient and dry feel characteristics of the skin. The feruloyl glycerides of the present invention protect colored hair from sun bleaching (i.e. elimination of the color producing chromophore in oxidized dye, such as paraphenylenediamine, plus peroxide), and add conditioning benefits and light reflection to hair. The feruloyl glycerides also help prevent the photodamage that causes all hair types to develop undersirable combing properties after UV exposure. This damage is frequently observed in the cuticle (outer skin of hair fiber) of the hair fiber. The prevention of photodamage to gray hair swatches can be observed in combing force of treated and control hair tresses, contact angle measurements, and preserving tryptophan, a key amino acid that decomposes on exposure to UV radiation. The feruloyl glycerides of the present invention protect lips, skin and hair against environmental damage, and create a synergistic effect with many other cosmetic and over-the-counter ("OTC") ingredients.

In the above paragraph, we indicated that the feruloyl glycerides have excellent solvent characteristics. This solvency is shown in the following phospholipid vitamin complex lotions. 1) A clear solution of 10% cholesterol powder in 90% feruloyl soy glyceride, 2) A set of clear solutions of 10% Vitamins E, A, D3, F (gamma linolenic acid) and 90% feruloyl soy glycerides 3) A set of clear solutions comprising 10% Uniqema's "Arlasilk™ Phospholipid EFA [Linoleamidopropyl PG-Dimonium Chloride Phosphate] and 90% feruloyl soy glycerides, 4) A series of solutions containing OTC sunscreens Avobenzone (3%), Benzophenone (5%), Octyl salicylate (4%), Octyl methoxycinnamate (7.5%), Octocrylene (10%) and q.s (quotient sufficient to make 100%) with feruloyl soy glycerides. All solutions remained stable for more than 3 months at 75F.

Manufacturing Procedure: (for All of the Formulations Listed Below)

In general, add Phase A components to main batch tank. Mix using a high shear mixer (e.g. a Lightning Mixer No. 4). Sprinkle thickener (if any) into vortex, created by a mixer. Mix until particles are dissolved or dispersed, while heating to 55° C. The feruloyl glyceride in the following examples comprised a family of feruloyl glycerides made from soy. It will be recognized that any feruloyl glyceride derived from any source or in any manner is encompassed within this invention. Feruloyl glyceride can be added to the oil phase ingredients in phase B, in a suitably sized premix vessel, heated and/or mixed until dissolved and/or dispersed, and then added to the main batch (phase A) with mixing.

Heat Phase B to 55° C., with mixing. When particles are dissolved, add Phase B to Phase A with vigorous mixing.

Turn on slow sweep and cool batch to 40° C., add other Phases.

Sample to Quality Control for review and approval at 25° C.

Feruloyl glyceride is an oil based component and has an oily feel at room temperature. Feruloyl glyceride is not water soluble, and it can act as a solvent for ingredients that are difficult to dissolve in water. In some embodiments, it may be desirable to suspend feruloyl glyceride within a matrix of emulsion or gel.

In some embodiments, it may be desirable to obtain an emulsion comprising feruloyl glyceride using a suitable emulsifier. In some embodiments, it may be desirable to incorporate such an emulsion in a final product that has a desired viscosity, and to achieve such a desired viscosity, a suitable viscosity modifier may be used. An emulsifier and/or viscosity modifier and/or surfactant can be a topically acceptable agent that is different from the linker agent or the compound comprising at least one UV-absorbing chromophore.

The pH of the final product comprising feruloyl glyceride can be any acceptable pH that is compatible with the purpose of the final product. For example, but not by way of limitation, when the final product is to be applied to the skin or hair, the pH range can be about 2.5 to about 9.0. For example, but not by way of limitation, when the final product is a shampoo, the pH range can be about 6.0 to about 8.0. For example, but not by way of limitation, when the final product is a moisture skin care product, the pH range can be about 4.0 to about 6.0. For example, but not by way of limitation, when the final product is an exfoliant and/or hair conditioner, the pH range can be about 2.0 to about 4.0. The final product can be hypoallergenic.

EXAMPLE 1

Phospholipid Vitamin Complex Lotion

| Phase | Wt. % | Ingredient |
|---|---|---|
| A | 69.5 | Water |
| A | 2.0 | Hydroxyethylcellulose (a viscosity modifier) |
| A | 5.0 | Glycerin (a skin emollient) |
| A | 2.8 | Ascorbic Acid (Vitamin C) (an antioxidant) |
| A | 0.1 | Phytonadione (Vitamin K) (an antioxidant) |
| A | 0.1 | Biotin (Vitamin B7) (an antioxidant) |
| B | 3.0 | Stearyl Alcohol (a stabilizer and for thickening the oil phase) |
| B | 2.0 | Glyceryl Stearate (a stabilizer and for thickening the oil phase) |
| B | 0.5 | Squalane (a skin emollient) |
| B | 0.5 | Olive Oil Amidopropyl Phosphatidyl PG-Dimonium Chloride (an emulsifier, also comprising what is sometimes called an essential fatty acid ("EFA") of a phospholipid |
| B | 3.0 | Tocopherol Acetate (Vitamin E) |
| B | 0.5 | Retinyl Palmitate (Vitamin A) |
| B | 0.5 | Cholecaliferol (Vitamin D3) |
| B | 0.5 | Linoleic Acid (Vitamin F) |
| B | 2.0 | PEG-40 Stearate (an emulsifier) |
| B | 5.0 | Feruloyl Glyceride |
| B | 0.1 | Ubiquinone 50 (Coenzyme Q10) (an antioxidant) |
| B | 1.0 | Cyclomethicone (a smoothing agent and a component that provides water resistance so final product does not undesirably wash off skin easily) |
| B | 0.9 | Steareth-20 (an emulsifier) |
| C | 0.2 | Fragrance |
| D | 0.3 | Water |
| D | 0.3 | Phenoxyethanol (a preservative) |
| D | 0.2 | Methylparaben (a preservative) |
| | 100.00 | |

It is well known that certain vitamins and amino acids are referred to as "essential" in nutritional products, since the body does not make these materials and one must include them in one's diet. In topically applied products they are equally important. Both Vitamin E and C are well known for their antioxidant properties within the skin and also for the fact that they work together in maintaining a natural defense against radicals. There is a significant amount of scientific evidence that the combination of Vitamin E and C significantly reduced the sunburn reaction to UVb irradiation. There is also evidence of the benefit of applying Vitamin D3 to the skin. The feruloyl glycerides of the present invention are excellent solvents for cholesterol and its derivatives which are excellent skin conditioning agents. Vitamin D3 is easily solubilized as well as other antioxidants, such as Coenzyme Q-10 [ubiquinone] or Superoxide Dismutase. If desired, a chelating agent, e.g., ethylenediamine tetraacetic acid ("EDTA"), can be added in the above example, and a corresponding amount of water can be reduced if a chelating agent (often in solution) is added.

In pre-sun and post-sun applications during a weekend, panelists treating one arm with the cream described above and a second arm with a similar control cream without the feruloyl glycerides of the present invention. When compared side by side, the arms treated with the feruloyl glycerides of the present invention had far less sunburn and blistering versus the control arm. All panelists verified that they had spent a minimum of 4 total hours in the sun on Saturday and Sunday.

In the above example, it is estimated that the SPF in the control was about 2-4, and that the SPF of the product containing feruloyl glycerides in accordance with the invention was about 7-10.

EXAMPLE 2

Water Resistant Sunscreen with Feruloyl Glycerides

| Phase | Wt. % | Ingredient |
|---|---|---|
| A | 51.40 | Deionized Water |
| A | 1.50 | Butylene Glycol (an emollient) |
| A | 0.20 | Carbomer 940 (a viscosity modifier) |
| B | 7.50 | Octinoxate (a sunscreen) |
| B | 6.00 | Oxybenzone (a sunscreen) |
| B | 5.00 | Octisalate (a sunscreen) |
| B | 10.00 | Octocrylene (a sunscreen) |
| B | 8.00 | Feruloyl Glyceride |
| B | 1.50 | PEG 40 Stearate (an emulsifier) |
| B | 0.50 | Steareth 20 (an emulsifier) |
| C | 5.00 | Deionized Water |
| C | 0.30 | Triethanolamine (a component that acts to neutralize Carbomer 940) |
| D | 2.00 | Acrylates/C12-22 Alkylmethacrylate Copolymer (a component that provides water resistance so final product does not undesirably wash off skin easily) |
| E | 0.60 | Propylene Glycol and/or Iodopropynyl Butylcarbamate (Liquid Germal Plus) (preservataives) |
| E | 0.50 | Phenoxyethanol and/or Isobutylparaben and/or Isopropylparaben and/or Butylparaben (Liquapar Optima) (preservatives) |

The feruloyl glycerides of the present invention are especially well suited to solubilizing sunscreens. Many of these sunscreen ingredients are known to form a powder after skin application as an emulsion and drying. This crystal formation causes a loss in UVb protection as the sunscreens simply flake off after drying.

The presence of feruloyl glycerides solubilize all oil soluble sunscreens and create a low melting eutectic which insures that the sunscreens remain fluid, are absorbed into the skin and will not powder on dry down. This provides products with longer lasting sun protection.

In side-by-side comparison testing, the formulation containing feruloyl glycerides provided longer lasting sun protection than the same formulation that did not contain feruloyl glycerides.

EXAMPLE 3

Lasting Color Hair Conditioner with Feruloyl Glycerides

| Phase | Wt. % | Ingredient |
|---|---|---|
| A | 80.0 | Deionized Water |
| A | 0.5 | Carbomer 940 (a viscosity modifier) |
| B | 0.2 | Isostearamidopropyl Ethydimonium Ethosulfate (a hair conditioner |

-continued

Lasting Color Hair Conditioner with Feruloyl Glycerides

| Phase | Wt. % | Ingredient |
|---|---|---|
| B | 0.3 | Soyamidopropyl Ehydimonium Ethosulfate (a hair conditioner) |
| B | 3.0 | Feruloyl Glycerides |
| B | 2.0 | Polyquaternium 11 (a hair conditioner) |
| B | 1.5 | PEG 100 Stearate (an emulsifier) |
| B | 1.0 | Self Emulsifying Glyceryl MonoStearate (an emulsifier) |
| C | 0.7 | Triethanolamine a component that acts to neutralize Carbomer 940) |
| C | 10.0 | Deionized Water |
| C | 0.5 | Imidazolidinyl Urea (a preservative) |

The feruloyl glycerides of the present invention add excellent conditioning properties to hair conditioner formulations. They are readily absorbed into porous hair which has been treated with chemical services (hair coloring, bleaching, permanent waves, straightening, etc.). After dry down, the hair exhibits excellent shine and luster, manageability and feels silky smooth. The feruloyl glycerides of the present invention are excellent additives for enhancing the long lasting hair colors that are perceived in permanent dyes. They do this by protecting the synthetic hair color from air oxidation and absorb both UVa and UVb ultraviolet rays which damage the color and eliminate the color producing chromophore.

In one test, hair swatches were colored with one of two commercially available permanent hair coloring products for medium ash brown. Some hair swatches were then wrapped in foil, while other hair swatches were either treated with a conditioner that contained feruloyl glycerides in accordance with the above formulation, or a control formulation that did not contain feruloyl glycerides. The non-foiled hair swatches were then exposed to northern sunlight for 32 hours and then compared to the hair swatches that had been foiled. The hair swatches that had been treated with a conditioner that contained feruloyl glycerides in accordance with the above formulation were much closer in color to the foiled hair swatches than the control formulation that did not contain feruloyl glycerides.

EXAMPLE 4

Lip Protector/Lip Stick

| Phase | Wt. % | Ingredient |
|---|---|---|
| A | 49 | Castor Oil (a diluent) |
| A | 10 | Feruloyl Glycerides |
| A | 8 | Beeswax (a wax component to build stick structure) |
| A | 4 | Carnauba Wax (a wax component to build stick structure) |
| A | 5 | Candelilla Wax(a wax component to build stick structure) |
| A | 1 | Ozokerite Wax(a wax component to build stick structure) |
| A | 10 | Isopropyl Myristate (an emollient) |
| A | 5 | Dimethicone (a silicone to provide shine) |
| A | 8 | Color Grind of Pigments and Castor Oil (an optional component if color is desired) |

A major site of sun damage and premature aging is the lip area. The feruloyl glycerides of the present invention show excellent compatibility with lipstick ingredients and provide emolliency, absorption, environmental protection (sun and wind damage), and prevention of transdermal moisture loss.

In one test, lips were treated with feruloyl glycerides in accordance with the above formulation, and separately treated at a different time with a control formulation that did not contain feruloyl glycerides. Lips that had been treated with feruloyl glycerides in accordance with the above formulation felt better than lips that had been treated with the control formulation that did not contain feruloyl glycerides.

EXAMPLE 5

Extra Moisturizing, Anti-Aging Shave Cream

| Phase | Wt. % | Ingredient |
|---|---|---|
| A | 6.00 | Stearic Acid (for soap formation in combination with Triethanolamine) |
| A | 1.00 | Coconut Acid (for soap formation in combination with Triethanolamine) |
| A | 1.00 | Laureth 4 (an emulsifier) |
| A | 2.00 | Mineral Oil (an emollient) |
| A | 4.00 | Feruloyl Glycerides |
| A | 3.00 | Isostearyl Neopentanoate (an emollient) |
| B | 60.0 | Demineralized Water |
| B | 5.0 | Glycerin (an emollient) |
| B | 8.0 | Ammonium Lauryl Sulfate (a surfactant) |
| B | 2.0 | Cocamidopropyl Betaine (a surfactant) |
| B | 2.0 | Acrylates/Octylacrylamide Copolymer (a viscosity modifier) |
| B | 4.8 | Triethanolamine (neutralizes stearic acid and coconut acid and for forms a soap with each) |
| C | 1.0 | Propylene Glycol and/or Methylparaben and/or Propylparaben (preservatives) |
| D | 0.2 | Fragrance |
|  | 100 |  |

Some skin specialists have viewed daily shaving as an exercise in daily exfoliation of the skin. When looked at shaving in this manner, one is not only removing the daily beard, but is also eliminating much of the stratum corneum cells on the skin's surface. This exposes the new skin surface to unprotected UVb and UVa exposure everyday after shaving. The presence of feruloyl glycerides of the present invention in a shaving preparation insures some skin absorption of this powerful antioxidant at the beginning of each day, thereby reducing environmental damage to the skin.

Panelists preferred the above shaving formulation containing feruloyl glycerides over a shaving control formulation that did not contain feruloyl glycerides.

EXAMPLE 6

Skin Lightener Formulations

The feruloyl glycerides of the present invention may be used in skin lightener formulations that carry other active ingredients into the epidermis and thus slow the melanin formation process in age spots. A formulation can be prepared using the formulation of Example 2, adding 1.5% Kojic acid, and reducing the amount of water a corresponding amount, i.e., reduce the amount of water by 1.5%. Kojic acid can be part of Phase B. Kojic acid can penetrate the epidermis and help reduce the production of melanin.

In one test, a formulation containing feruloyl glycerides was applied to one area of skin having age spots, and a control formulation not containing feruloyl glycerides was applied to another area of skin having age spots. Panelists preferred the formulation containing feruloyl glycerides over the control formulation. Viewing the skin areas after 28 days, 56 days and 84 days showed that skin areas treated with the formulation containing feruloyl glycerides were lighter in color than the skin areas that had been treated with the control formulation.

EXAMPLE 7

Anti-Aging Stick Protector

The feruloyl glycerides of the present invention may be incorporated into an anti-aging stick protector to carry peptides into the skin, calling for maximum production of collagen and elastin proteins and minimizing premature degradation of these skin tightening support proteins. Anti-Aging formulations may protect the skin from UVa irradiation from normal sunlight, may alter the skin's moisture retentive characteristics, may add to the skin luminescence, may prevent the excess formation of melanin containing age spots, and may prevent the formation of radicals from UVb and UVa, which then react with other skin ingredients to alter its natural flexibility and tightness. The manufacturing process can involve addition of the liquids to the main batch kettle with mixing. Heat from a jacket kettle can be turned on and the solid ingredients can be added one at a time, until the complete system is melted and solubilized and/or fully dispersed. The hot liquid can then poured in suitable stick molds and allowed to cool and solidify.

Anti-Aging Stick

| Phase | % | Ingredient |
|---|---|---|
| A | 40.25% | Castor oil (a diluent) |
| A | 20% | Feruloyl Soy Glycerides |
| A | 10% | Isopropyl Myristate (an emulsifier) |
| A | 9.0 | Octycrylene (a sunscreen) |
| A | 3.0 | Avobenzone (a sunscreen) |
| A | 7.0 | Octyl methoxycinnamate (a sunscreen) |
| A | 5.0 | Candelilla Wax (a was to build a stick structure) |
| A | 1.0 | Carnauba Wax (a was to build a stick structure) |
| A | 0.75 | Ozokerite Wax (a was to build a stick structure) |
| A | 4.0 | Beezwax (a was to build a stick structure) |
|  | 100% |  |

Panelists preferred the formulation containing feruloyl glycerides over a control formulation that did not contain feruloyl glycerides. This product is particularly useful to protect skin around the eyes, the skin of the nose, and other portions of the face from sunlight.

EXAMPLE 8

Dental Cleanser

The feruloyl glycerides of the present invention may be incorporated into a dental cleanser to solubilize dental stains and to flush them away, for example, as part of a dental paste or mouthwash.

Dental Gel

| Phase | % | Ingredients |
|---|---|---|
| A | 1.0 | Carboxymethyl cellulose (a thickener) |
| A | 3.0 | Feruloyl Soy Glycerides |
| A | 60 | Sorbitol (a diluent and sweetener) |
| A | 11.4 | Water |
| A | 5 | Sodium Saccahrin (a sweetener) |

-continued

Dental Gel

| Phase | % | Ingredients |
|---|---|---|
| A | 8 | Sodium Silicate (a thickener) |
| A | 10 | Sodium Silicate (an abrasive, with larger particles than the sodium silicate used as a thickener) |
| A | 1.0 | Flavor |
| A | 0.6 | Sodium Lauryl Sulfate (dental grade cleanser, .e.g, a dental grade cleanser without a soapy taste) |

Panelists preferred the formulation containing feruloyl glycerides over a control formulation that did not contain feruloyl glycerides.

EXAMPLE 9

Co-Solvent for Fragrances

The feruloyl glycerides of the present invention may be used as co-solvent in fragrance compounding. When creating fragrances, perfumers draw on thousands of scented and fixing compounds which complex with other ingredients within the perfume formulation to achieve the ultimate fragrance interpretation that is desired. The science of perfumery is thousands of years old and normally requires an apprenticeship of 5 years or more with a Master Perfumer to receive accreditation by the American Society of Perfumers. The basic construction of fragrances includes 3 divisions within the fragrance. These are referred to as top, middle and bottom notes. The top notes are light, delicate and quickly volatize at room temperature. The middle notes have more body and require more heat and energy to lift from the skin. The bottom notes of a fragrance form its foundation. They are the heavy lasting notes. Holding the top, middle and bottom notes together involves the science of fixatives. A well-balanced fragrance normally presents itself as a well-balanced bouquet with strong foundation notes, middle statements and sparkles of unexpected top notes. While this is generally true, the opposite is often an unexpected pleasure as in the classic Channel™ No. 5 fragrance, which is mostly sparkling top notes, with moderate to slight base notes.

Within every fragrance the choice of solvent (or several co-solvents) often plays a critical role in the fragrances stability, application characteristics and lasting power. Typical fragrance ingredients (remember there are thousands to choose from) include terpineol, linalool, benzyl alcohol, benzaldehyde, ylang-ylang and so on. To hold all of these 25-100 ingredients together in a stable solution is no small task. Many times the perfumer feels that they have a stable solution but then there is a formation of one crystal, then another and quickly an avalanche of components falling from what was a clear solution.

Diethyl phthalate (DEP), Dioctyl adipate (DOA), and Propylene Glycol are three of the most common solvents used in perfumery by perfumers. The feruloyl glycerides of the present invention bring a totally new dimension to the science of perfumery. It is a useful solvent that takes a broad variety of hydrophobic and some slightly hydrophilic materials into solution. The feruloyl glycerides of the present invention have shown possibilities of forming clathrate structures around fragrances and individual components, which will enhance their stability, performance and resistance to attack. Being a partial triglyceride, fatty acid ester and ferulic acid ester we see an unexpected synergy of solvent properties, antioxidant characteristics, UVa & b absorbance qualities, skin absorption characteristics, surface activity, and addition to structural type delivery. Fragrances can be made into alcohol solutions, gels, solids, etc. They can be positioned as providing health benefits, anti-aging benefits, environmental protectants, sun protection fragrances as well as many other characteristics. With some hydroxyl substitution and/or ethoxylation on the triglyceride moieties, the molecule can solubilize and/or emulsify hydrophilic materials.

Panelists found that the formulation containing feruloyl glycerides performed just as well in terms of fragrance stability, application characteristics and lasting power as a control formulation that contained DEP instead of feruloyl glycerides. And, a formulation containing DEP does not provide the same UV protection and anti-aging attributes as a formulation containing feruloyl glycerides.

In accordance with the invention the amount of feruloyl glyceride (which is a combination of a linker agent and a compound comprising at least one UV-absorbing chromophore) in a product for topical application as described above can be any suitable range, but is typically about 10% by weight or less of the product. In one preferred embodiment, the amount of the combination of a linker agent and a compound comprising at least one UV-absorbing chromophore in a product for topical application is in the range of about 3% to 10% by weight. For a phospholipid vitamin complex lotion, the amount of a combination of a linker agent and a compound comprising at least one UV-absorbing chromophore is preferably about 5% by weight. For a water resistant sunscreen, the amount of a linker agent and a compound comprising at least one UV-absorbing chromophore is preferably about 8% by weight. For a hair conditioner, the amount of a combination of a linker agent and a compound comprising at least one UV-absorbing chromophore is preferably about 3% by weight. For a lip protector and/or lip stick, the amount of a combination of a linker agent and a compound comprising at least one UV-absorbing chromophore is preferably about 10% by weight. For a shave cream, the amount of a combination of a linker agent and a compound comprising at least one UV-absorbing chromophore is preferably about 4% by weight. In each event the resultant combination incorporates topically acceptable agents other than the linker agent/chromophore such as for feruloyl glyceride in an amount of about 90% by weight or more. The resultant combination comprises a synergistic mixture which is favored and efficacious relative to mixtures which are absent the linker agent/chromophore combination (e.g., feruloyl glyceride).

The embodiments of the invention, and the invention itself, are now described in such full, clear, concise and exact terms to enable a person of ordinary skill in the art to make and use the invention. To particularly point out and distinctly claim the subject matters regarded as invention, the following claims conclude this specification. To the extent variations from the preferred embodiments fall within the limits of the claims, they are considered to be part of the invention, and claimed.

We claim:

1. A vitamin complex lotion comprising: water; hydroxyethylcellulose; glycerin; ascorbic acid; phytonadione; biotin; stearyl alcohol; glyceryl stearate; squalane; olive oil amidopropyl phosphatidyl PG-dimonium chloride; tocopherol acetate; retinyl palmitate; cholecalciferol; linoleic acid; PEG-40 stearate; a UV-absorbing compound; ubiquinone 50; cyclomethicone; Steareth-20; fragrance; phenoxyethanol; and methylparaben, wherein the UV-absorbing compound comprises a linker agent having the general formula:

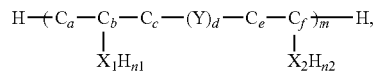

wherein:

$X_1$ and $X_2$ are the same or different, and at least one of $X_1$ or $X_2$ is a functional group bound with ferulic acid, and $b+f \geq 2$;

Y comprises an O, N, or S that is substituted or unsubstituted;

each a, b, c, e and f is $\geq 0$ and $a+b+c+e+f \geq 2$;

d is 1;

n1 and n2 represent the number of hydrogen atoms required to complete the undesignated valencies; and m ranges from 1 to about 100 and each individual m unit may be the same or different.

2. The vitamin complex lotion of claim 1, wherein the lotion comprises: approximately 69.8 wt. % water; approximately 2.0 wt. % hydroxyethylcellulose; approximately 5.0 wt. % glycerin; approximately 2.8 wt. % ascorbic acid; approximately 0.1 wt. % phytonadione; approximately 0.1 wt. % biotin; approximately 3.0 wt. % stearyl alcohol; approximately 2.0 wt. % glyceryl stearate; approximately 0.5 wt. % squalane; approximately 0.5 wt. % olive oil amidopropyl phosphatidyl PG-dimonium chloride; approximately 3.0 wt. % tocopherol acetate; approximately 0.5 wt. % retinyl palmitate; approximately 0.5 wt. % cholecalciferol; approximately 0.5 wt. % linoleic acid; approximately 2.0 wt. % PEG-40 stearate; approximately 5.0 wt. % UV-absorbing compound; approximately 0.1 wt. % ubiquinone 50; approximately 1.0 wt. % cyclomethicone; approximately 0.9 wt. % Steareth-20; approximately 0.2 wt. % fragrance; approximately 0.3 wt. % phenoxyethanol; and approximately 0.2 wt. % methylparaben.

3. A vitamin complex lotion comprising at least one vitamin and a UV-absorbing compound, wherein the UV-absorbing compound comprises a linker agent having the general formula:

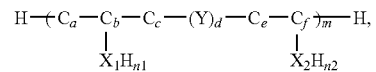

wherein:

$X_1$ and $X_2$ are the same or different, and at least one of $X_1$ or $X_2$ is a functional group bound with ferulic acid, and $b+f \geq 2$;

Y comprises an O, N, or S that is substituted or unsubstituted;

each a, b, c, e and f is $\geq 0$ and $a+b+c+e+f \geq 2$;

d is 1;

n1 and n2 represent the number of hydrogen atoms required to complete the undesignated valencies; and m ranges from 1 to about 100 and each individual m unit may be the same or different, and wherein the amount of UV-absorbing compound is about 5% by weight.

4. The vitamin complex lotion of claim 3, further comprising Vitamin C, wherein the amount of Vitamin C is about 2.8% by weight.

5. The vitamin complex lotion of claim 3, further comprising Vitamin K, wherein the amount of Vitamin K is about 0.1% by weight.

6. The vitamin complex lotion of claim 3, further comprising Vitamin B7, wherein the amount of Vitamin B7 is about 0.1% by weight.

7. The vitamin complex lotion of claim 3, further comprising Vitamin E, wherein the amount of Vitamin E is about 3.0% by weight.

8. The vitamin complex lotion of claim 3, further comprising Vitamin A, wherein the amount of Vitamin A is about 0.5% by weight.

9. The vitamin complex lotion of claim 3, further comprising Vitamin D3, wherein the amount of Vitamin D3 is about 0.5% by weight.

10. The vitamin complex lotion of claim 3, further comprising Vitamin F, wherein the amount of Vitamin F is about 0.5% by weight.

* * * * *

UNITED STATES PATENT AND TRADEMARK OFFICE
CERTIFICATE OF CORRECTION

PATENT NO. : 7,744,856 B2  Page 1 of 1
APPLICATION NO. : 11/771843
DATED : June 29, 2010
INVENTOR(S) : Louis J. Defilippi et al.

It is certified that error appears in the above-identified patent and that said Letters Patent is hereby corrected as shown below:

Title Page, under item 73 Assignee:
Please replace "Biotech" with --Biotechnology--.

Signed and Sealed this

Twelfth Day of October, 2010

David J. Kappos
*Director of the United States Patent and Trademark Office*

UNITED STATES PATENT AND TRADEMARK OFFICE
CERTIFICATE OF CORRECTION

PATENT NO.        : 7,744,856 B2                                          Page 1 of 1
APPLICATION NO.   : 11/771843
DATED             : June 29, 2010
INVENTOR(S)       : Louis J. DeFilippi et al.

It is certified that error appears in the above-identified patent and that said Letters Patent is hereby corrected as shown below:

In Title Page, under Assignee:
        Please replace "Biotech" with --Biotechnology--.

Signed and Sealed this

Ninth Day of November, 2010

David J. Kappos
*Director of the United States Patent and Trademark Office*